United States Patent
Harvey

(10) Patent No.: US 11,117,847 B1
(45) Date of Patent: Sep. 14, 2021

(54) HIGH DENSITY TURBINE AND DIESEL FUELS DERIVED FROM ADAMANTANE

(71) Applicant: The United States of America, as Represented by the Secretary of the Navy, Arlington, VA (US)

(72) Inventor: Benjamin G. Harvey, Ridgecrest, CA (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 16/369,829

(22) Filed: Mar. 29, 2019

Related U.S. Application Data

(60) Provisional application No. 62/649,922, filed on Mar. 29, 2018.

(51) Int. Cl.
| | | |
|---|---|---|
| *C07C 2/74* | (2006.01) | |
| *C07C 7/14* | (2006.01) | |
| *C07C 7/04* | (2006.01) | |
| *C07C 7/00* | (2006.01) | |
| *C07C 13/615* | (2006.01) | |
| *C10L 1/08* | (2006.01) | |

(52) U.S. Cl.
CPC ............... *C07C 2/74* (2013.01); *C07C 7/005* (2013.01); *C07C 7/04* (2013.01); *C07C 7/14* (2013.01); *C07C 13/615* (2013.01); *C10L 1/08* (2013.01); *C07C 2603/74* (2017.05); *C10L 2270/026* (2013.01); *C10L 2270/04* (2013.01); *C10L 2290/543* (2013.01); *C10L 2290/544* (2013.01)

(58) Field of Classification Search
CPC .. C07C 2/74; C07C 7/04; C07C 7/005; C07C 7/14; C07C 13/615; C07C 2603/74; C10L 1/08; C10L 2290/544; C10L 2270/026; C10L 2290/543; C10L 2270/04
See application file for complete search history.

(56) References Cited

U.S. PATENT DOCUMENTS

| | | | | |
|---|---|---|---|---|
| 3,382,288 | A * | 5/1968 | Schneider | C07C 2/54 585/352 |
| 3,646,233 | A * | 2/1972 | Moore | C07C 13/615 585/22 |
| 3,928,480 | A * | 12/1975 | Tabushi | C07C 2/54 585/352 |
| 5,043,503 | A * | 8/1991 | Del Rossi | C07C 2/54 585/360 |
| 5,345,020 | A * | 9/1994 | Shen | C07C 2/54 585/352 |
| 2008/0319241 | A1* | 12/2008 | Huang | C07C 13/615 585/21 |
| 2015/0011810 | A1* | 1/2015 | Harvey | C07C 5/2506 585/22 |
| 2015/0344385 | A1* | 12/2015 | Huang | C07C 5/29 585/352 |

* cited by examiner

*Primary Examiner* — Ali Z Fadhel
(74) *Attorney, Agent, or Firm* — Naval Air Warfare Center Weapons Division; Stuart H. Nissim

(57) ABSTRACT

In the present method a reaction mixture is comprised of a source of adamantane, mixed with an alkane or cycloalkane. A Lewis acid catalyst is added to the reaction mixture which is heated and then purified. The resulting alkyl diamondoid mixtures have significantly higher densities and volumetric net heats of combustion while maintaining low viscosities which allow for use at low temperature.

20 Claims, 4 Drawing Sheets

HIGH DENSITY TURBINE AND DIESEL FUELS DERIVED FROM ADAMANTANE

CROSS-REFERENCE TO RELATED APPLICATIONS

This is a non-provisional application, claiming the benefit of parent application Ser. No. 62/649,922 filed on Mar. 29, 2018, whereby the entire disclosure of which is incorporated herein by reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND

The invention describes a novel alkyl diamondoid mixture and a high-throughput method to synthesize high density alkyl diamondoid mixtures from adamantane. Such high density alkyl diamondoids can be used for fuels having higher volumetric net heats of combustion than conventional fuels. These fuels have applications as both turbine and diesel fuels, exhibiting densities greater than 0.9 g/mL and volumetric net heats of combustion at least 6% higher than conventional jet and diesel fuels.

BRIEF DESCRIPTION OF THE DRAWINGS

Features and advantages of examples of the present disclosure will be apparent by reference to the following detailed description and drawings.

Figure 1:
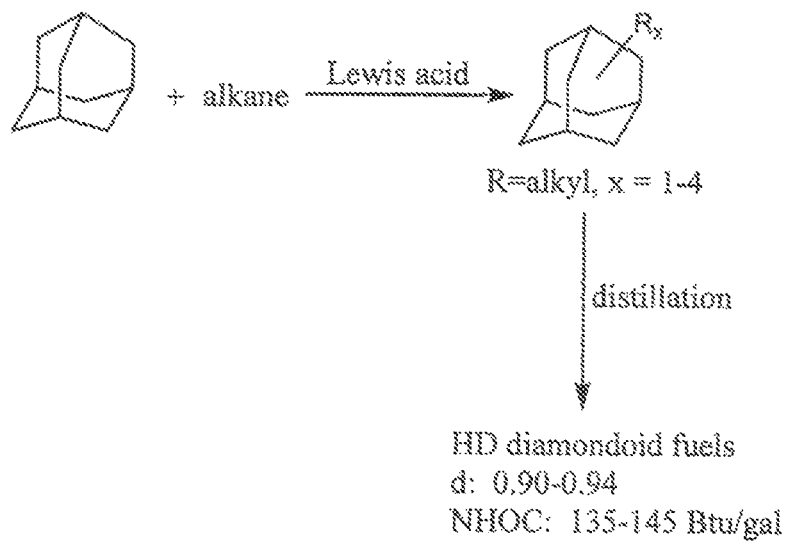
FIG. 1 is a flow chart showing a chemical scheme for the synthesis of alkyl adamantanes via alkylation with a Lewis acid catalyst, according to embodiments of the invention.

It is to be understood that the following detailed descriptions are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

For fuel, the volumetric net heat of combustion (NHOC) indicates the amount of heat energy that is released for a given volume of fuel that is burned. Fuel with a higher volumetric net heat of combustion releases more heat energy from a given volume of fuel than fuel with a lower volumetric net heat of combustion. For conventional jet fuel the volumetric net heat of combustion is around 125 kBtu/gal and for diesel fuel it is around 129 kBtu/gal.

Another observed property for diesel fuels is the cetane number. The cetane number measured for a fuel is inversely related to its ignition delay. Diesel fuels with higher cetane numbers (and shorter ignition delays) allow for more efficient fuel consumption, decreased emissions, and reduced engine knocking and wear.

High density hydrocarbons that combine dense multicyclic cores with pendent alkyl groups have applications as high performance jet and diesel fuels. The multicylic core increases the density of the molecule and leads to a higher volumetric net heat of combustion, while the alkyl chains can reduce the viscosity, lower the melting point, and increase the cetane number of the fuels. Diamondoids are an example of such multicyclic hydrocarbons.

Alkyl diamondoids (for example, alkyl-adamantanes) are very useful as high-performance fuels due to their high densities, lower freezing points, and lower viscosities. Alkyl diamondoids combine a tetracyclic fused cyclohexane core structure with alkyl groups of various lengths. Single component alkyl adamantane fuels, having an alkyl chain from ethyl to pentyl, exhibit densities ranging from 0.91 to 0.95 g/mL and NHOCs between 140 and 144 kBtu/gal; these properties are comparable to the high density missile fuel JP-10 (d=0.935 g/mL, NHOC=141.5 kBtu/gal). These alkyl diamondoids exhibit derived cetane numbers (DCNs) between 42 and 50, high enough for use in a conventional diesel engine. For example, 1-ethyl-3,5,7-trimethyladamantane (ETMA) has a DCN of 46.

Although simple alkyl diamondoids with alkyl groups larger than methyl can be readily synthesized by common organic chemistry techniques, preparation of these fuels on a commercial scale would require a higher throughput method that does not rely on the use of stoichiometric organometallic reagents, can be conducted under moderate conditions, and selectively generates fuel fractions that have applications as high density diesel and jet fuels. The method of the present invention provides these characteristics. The use of alkanes as the alkyl source in the method of the present invention is advantageous given their abundance, low cost, and the diversity of available substrates.

The present invention describes methods to synthesize high density diamondoid fuels with volumetric net heats of combustion at least more than about 6-10% higher than conventional petroleum-derived jet fuels, while maintaining cetane numbers high enough for combustion in conventional diesel engines, greater than about 40. These fuels can be used in a wide variety of aircraft, automobiles, trucks, unmanned vehicles, and ships with the ability to extend the range of these vehicles. The method of the present invention is a simple, high throughput process for the preparation of fuels via alkylation of adamantane with alkanes in the presence of at least one strong Lewis acid catalyst. The properties of the fuels can be controlled by the reaction conditions, the length of the alkane, and the strength of the Lewis acid catalyst. This flexibility allows for the generation of both turbine and diesel fuels. In particular fuels can be generated with densities >0.90 g/mL and having cetane numbers greater than 42.

In the present method a reaction mixture is comprised of a source of adamantane, including but not limited to adamantane, one or more alkyl adamantanes, or various combinations thereof, mixed with an alkane or cycloalkane having from 2-40 carbon atoms. In embodiments the alkane or cycloalkane has from 2-12 carbon atoms. In embodiments the alkane is n-hexane, n-heptane, n-octane, n-nonane, or n-decane. In other embodiments branched alkanes are used. In still other embodiments a complex mixture of alkanes is used including mineral spirits, naphtha, petroleum ether, kerosene, diesel fuel, vegetable or animal derived triglycerides or fatty acids, methyl esters, synthetic paraffinic kerosenes, hydrotreated fatty acids and esters, and related mixtures. In embodiments the alkane is added in a mole ratio of alkane:adamantane of from about 2:1 up to about 5:1. A Lewis acid is added to the reaction mixture. In embodiments 0.001-40 mol % of the Lewis acid is used. In embodiments the Lewis acid is selected from $AlCl_3$, $AlBr_3$, $AlI_3$, and metal or metalloid triflates. In other embodiments a heterogeneous acid is used. In still other embodiments a Lewis acidic ionic liquid is used resulting in a biphasic reaction medium.

Figure 1A:
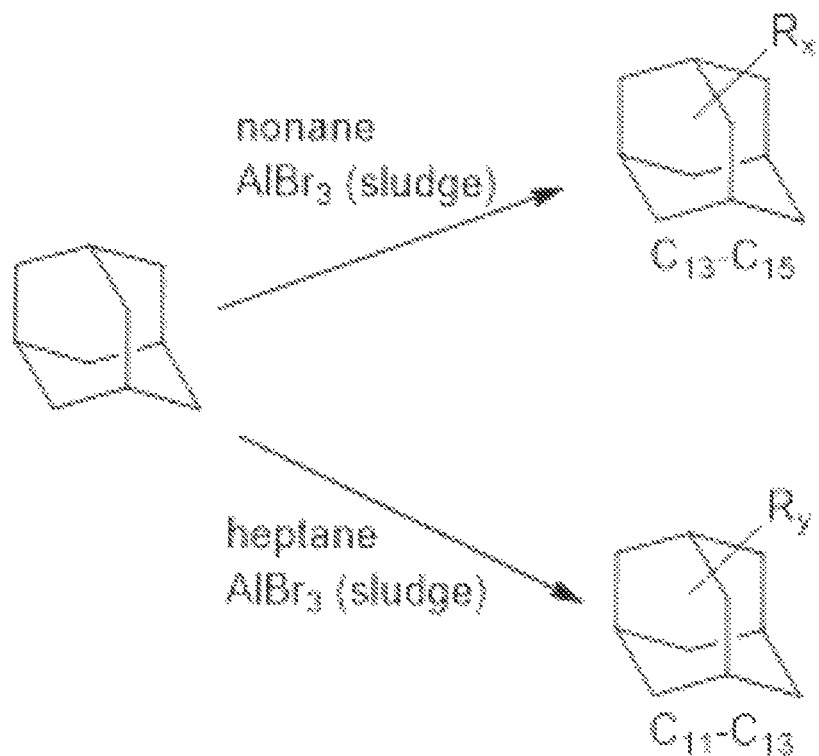
FIG. 1a is a flow chart showing a chemical scheme for the synthesis of alkyl adamantanes via alkylation using heptane or nonane with $AlBr_3$ as a catalyst, according to embodiments of the invention.

A general chemical scheme for the alkylation of adamantane is illustrated in FIG. 1; and in FIG. 1a a scheme depicting the use of heptane and nonane as the alkane is illustrated. In embodiments the present method comprises:

a) providing a reaction mixture by blending a source of adamantane with an alkane or alkane mixture and a Lewis acid;
b) heating this reaction mixture to generate a complex mixture of alkyl adamantanes;
c) removing residual alkanes via distillation; and
d) removing residual unreacted adamantane via distillation, crystallization, and/or sublimation.

In embodiments, additionally separating alkyl adamantane mixtures by fractional distillation to yield high density fuel blends.

To further illustrate the present disclosure, examples are given herein. It is to be understood that these examples are provided for illustrative purposes and are not to be construed as limiting the scope of the present disclosure.

EXAMPLES

Example 1: Preparing an Alkyl Adamantane Mixture

The alkane source is added to a source of adamantane in a molar ratio of about 2:1 up to about 5:1 (alkane:adamantane).

The reaction mixture is heated at a temperature ranging between about ambient and about 200° C. for a time period ranging from 10 minutes to 7 days. In embodiments the reaction is conducted in a temperature range from about 100-200° C. In embodiments the reaction is allowed to proceed until a desired degree of conversion is achieved. Higher temperatures and longer reaction times generally lead to cracking of intermediate products.

Residual alkane is then removed by distillation. In embodiments the distillation is conducted under reduced pressure. In other embodiments the residual alkane is removed along with residual adamantane via a fractional distillation process.

Residual adamantane is removed by methods including fractional distillation, sublimation, or crystallization. In embodiments solid alkyl adamantanes are removed by fractional distillation. In other embodiments adamantane and other solid alkyl adamantanes are removed by sublimation under reduced pressure. In other embodiments, mixtures are chilled to temperatures ranging from about 0 to −50 degrees C. to precipitate out adamantane and other solid alkyl adamantanes. The liquid adamantane mixture is then isolated by decantation or filtration. In embodiments the adamantane concentration is decreased to less than 10% of the product mixture. In other embodiments the adamantane is recycled to increase the overall conversion of adamantane to alkyl adamantanes.

Optionally, the alkyl adamantane mixture is fractionally distilled under reduced pressure to yield fuel mixtures. In embodiments product fuels contain $C_{10}$-$C_{12}$ or $C_{10}$-$C_{13}$ or $C_{10}$-$C_{14}$ or $C_{10}$-$C_{15}$ or $C_{10}$-$C_{16}$ or $C_{10}$-$C_{17}$ mixtures. After isolation of the fuel mixtures, heavier adamantanes can be isolated by high temperature vacuum distillation. These heavy adamantane fractions typically contain $C_{15}$-$C_{25}$ alkyl adamantanes.

In embodiments the alkyl adamantane fuels have densities ranging from about 0.90 to about 0.94 g/mL and volumetric net heats of combustion ranging from about 135.0 kBtu/gal to 145.0 kBtu/gal. In embodiments the alkyl adamantane fuels have cetane numbers ranging from about 42 to about 50.

Example 2: Preparing an Alkyl Adamantane Mixture

Referring to FIGS. 1 and 1a, the synthesis of the alkyl adamantane mixtures is conducted in a glass reactor at moderate temperature (~70° C.). In embodiments the Lewis acid catalyst $AlBr_3$ is utilized due to its excellent solubility in organic solvents. Under the reaction conditions employed, the alkane (either nonane or heptane) acted as both the solvent and reagent. Three equivalents of the alkane were used for each equivalent of adamantane. The mixture of the alkane and adamantane with $AlBr_3$ originally formed a heterogeneous mixture, but upon heating, all of the adamantane dissolved. The alkyl adamantane mixtures were purified by low temperature precipitation of unreacted adamantane followed by fractional vacuum distillation. In the resulting purified products only 4% adamantane remained in the mixture from nonane, and 7% adamantane remained in the mixture from heptane.

Example 3: Preparing an Alkyl Adamantane Mixture from Adamantane and Nonane (Non-Ad)

In a glass reactor $AlBr_3$ (44.8 g, 0.168 mol) was added to adamantane (80.0 g, 0.587 mol). The flask was equipped with a stir bar and nonane (224 g, 1.75 mol) was added. The mixture was heated under nitrogen to 70° C. (oil bath temperature) for 5 days. After cooling and decanting, the reaction mixture was extracted with diethyl ether and washed with deionized $H_2O$, aqueous sodium bicarbonate, and brine. The organic layer was then dried over sodium sulfate and concentrated under vacuum. Fractional vacuum distillation (~0.01 Torr) was carefully performed to remove residual alkanes and adamantane. The fraction distilling from 50-75° C. was collected. The mixture consisted of 96% alkyl adamantanes and 4% unreacted adamantane.

Figure 2:
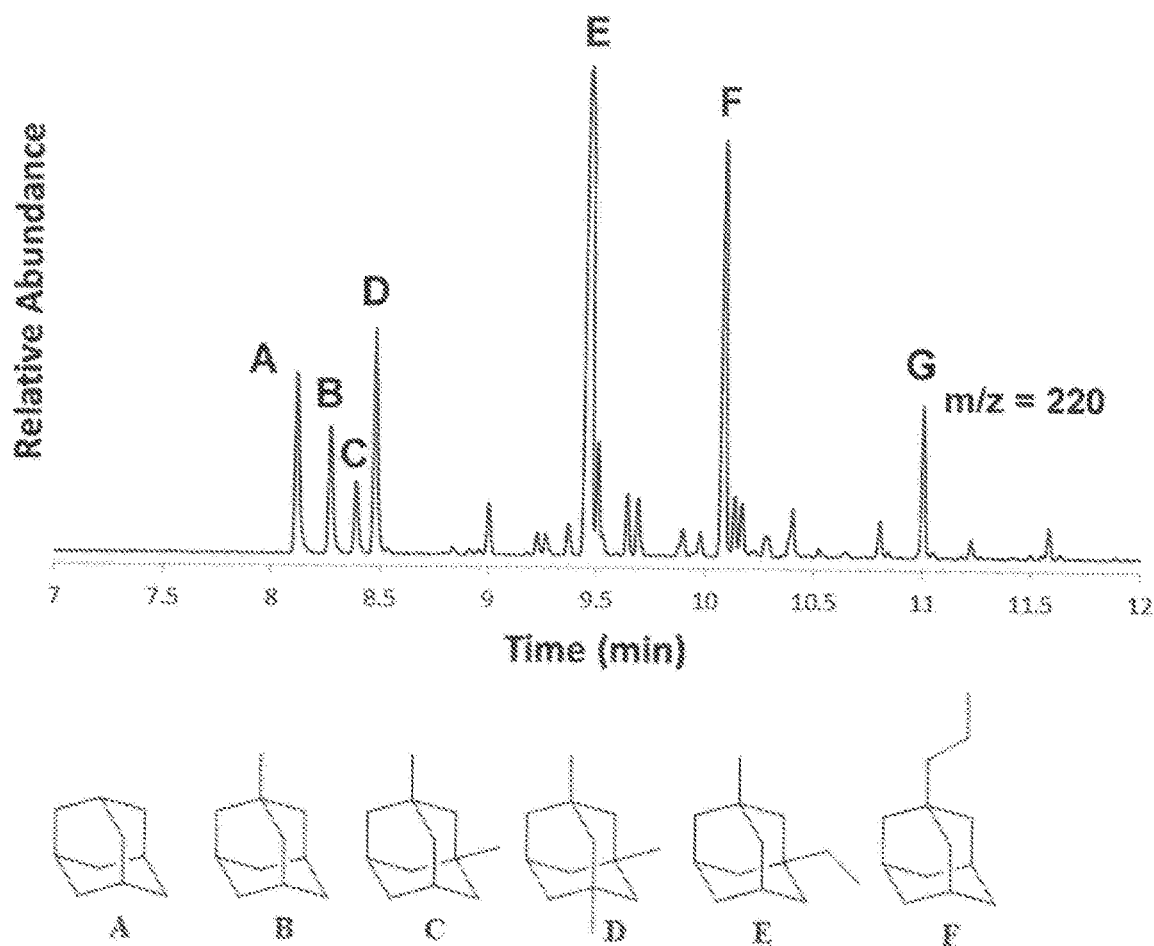
FIG. 2 is a gas chromatogram of a distilled mixture prepared via alkylation of adamantane with heptane, according to embodiments of the invention.

Some basic properties of the fuel mixture are included in Table 1, below. A GC chromatogram of the Non-Ad mixture is shown in FIG. 2.

Example 4: Preparing an Alkyl Adamantane Mixture from Adamantane and Heptane (Hept-Ad)

In a glass reactor, $AlBr_3$ (35.0 g, 0.131 mol) was added to adamantane (80.0 g, 0.587 mol). The flask was equipped with a stir bar and heptane (175 g, 1.75 mol) was added. The mixture was heated under nitrogen to 70° C. (oil bath temperature) for 5 days. After cooling and decanting, the reaction mixture was extracted with diethyl ether and washed with deionized H₂O, aqueous sodium bicarbonate, and brine. Residual alkanes were removed on a rotary evaporator, while adamantane was removed by fractional vacuum distillation. The organic layer was then dried over sodium sulfate and concentrated under vacuum. Fractional vacuum distillation (~0.01 Torr) was carefully performed to remove the excess hexane and adamantane. The product fraction, a colorless liquid, was distilled from 32 to 60° C. (0.01 Torr). The mixture consisted of 93% alkyl adamantanes and 7% unreacted adamantane.

Some basic properties of the mixture are included in Table 1, below. A GC chromatogram of the Hept-Ad mixture is shown in FIG. 3.

As shown in FIG. 2, the primary components of the fuel mixture derived from adamantane and heptane (Hept-Ad) were 1-ethyl-3-methyl adamantane (E) and 1-propyladamantane (F). Significant quantities of 1-methyladamantane (B), 1,3-dimethyladamantane (1,3-DMA) (C), and 1,3,5-dimethyladamantane (D) were also observed.

Figure 3:
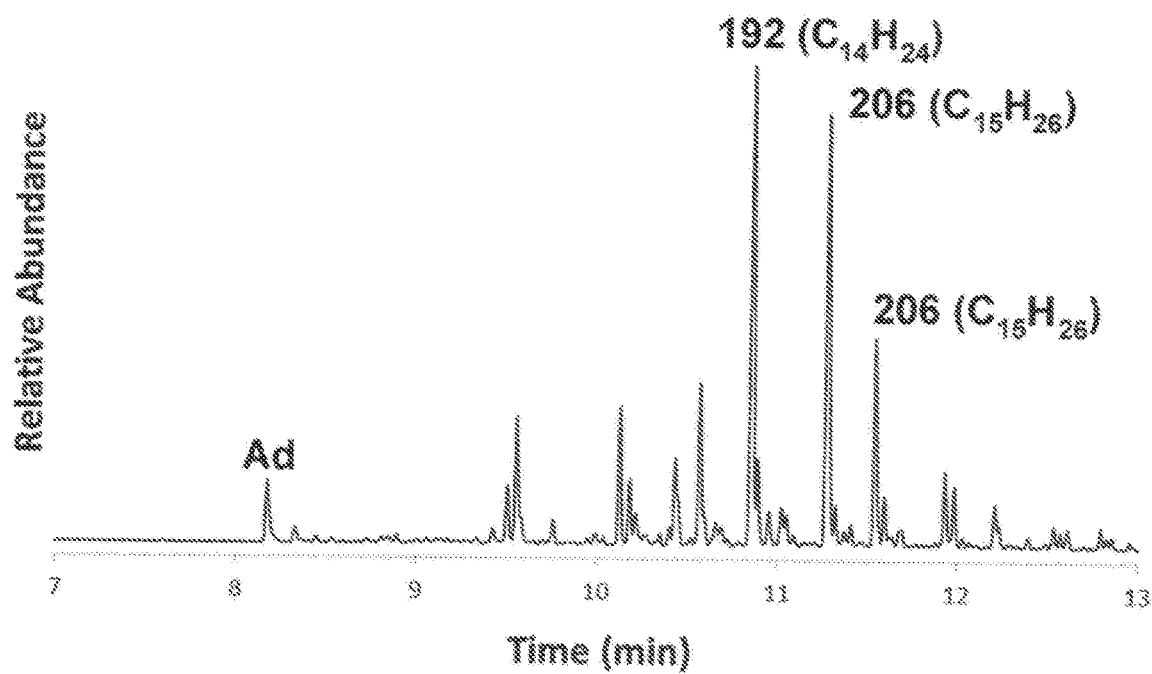
FIG. 3 is a gas chromatogram of a distilled mixture prepared via alkylation of adamantane with nonane, according to embodiments of the invention.
Figure 3:
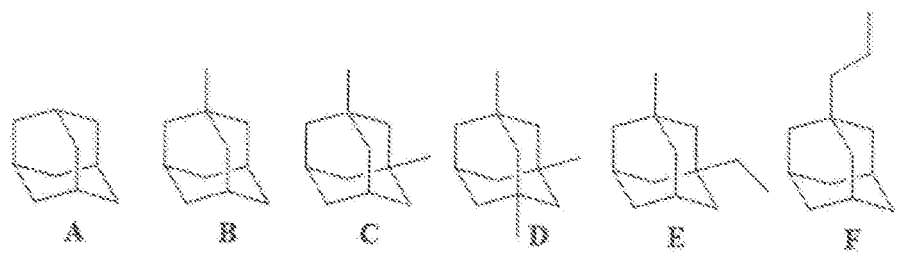

As shown in FIG. 3, the product distribution for Non-Ad was shifted to higher molecular weight molecules. In contrast to the heptane-sourced mixture, the nonane-sourced mixture (Non-Ad) contained virtually no 1-methyladamantane, 1,3-DMA, or 1,3,5-trimethyladmantane.

Heavier adamantanes were observed in both the Hept-Ad and Non-Ad crude reaction mixtures but were excluded from the fuel mixtures by fractional distillation, reducing the viscosity of the tested product fuels.

For both mixtures, no distinct melting point or freezing point was observed using differential scanning calorimetry (DSC) even at temperatures as low as −80° C. Similarly, there was no evidence of a glass transition temperature for either sample. Both mixtures were stored in a −30° C. freezer without any observable cloudiness or precipitation. This result is in contrast to single component alkyl diamondoid fuels. For example, 2-propyladamantane, which is a good surrogate for Hept-Ad, has a freezing point of −66° C. (cooling cycle, DSC) and a melting point of −32° C. (heating cycle, DSC). Similarly, Non-Ad can be compared to 1-pentyladamantane which exhibits a freezing point of −79° C. (cooling cycle, DSC) and a melting point of −22° C. (heating cycle, DSC). The structural diversity of Hept-Ad and Non-Ad depresses the freezing point of the fuel mixture. The adamantane fuel mixtures can also be compared to pure 1,3-dimethyladamantane (1,3-DMA) which has a freezing point of −28° C.

Figure 4:
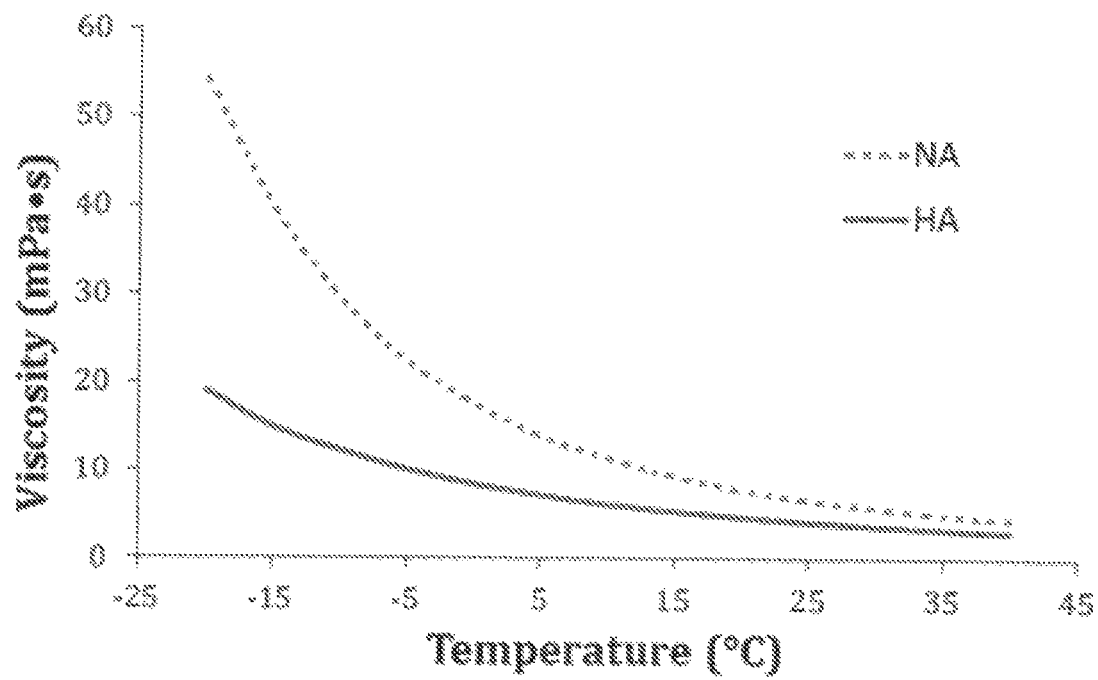
FIG. 4 is a graph illustrating the dynamic viscosity of alkyl adamantane mixtures from −20 to 40° C., according to embodiments of the invention.

Referring to FIG. 4, the dynamic viscosities of the current mixtures of Hept-Ad and Non-Ad were measured between −20 and 40° C. Hept-Ad exhibited a −20° C. dynamic viscosity of 19 mPa·s, more than 3.5 times lower than 2-propyladamantane with a −20° C. viscosity of 68 mPa·s. Non-Ad exhibited a −20° C. dynamic viscosity of 54 mPa·s, nearly three times that of Hept-Ad, but only about one half the viscosity of 1-pentyladamantane (100 mPa·s). The higher viscosity of Non-Ad compared to Hept-Ad is attributed to the higher average molecular weight of the molecules comprising Non-Ad.

The 40° C. viscosity of fuels is important for use in diesel engines. The range of acceptable 40° C. kinematic viscosities for diesel #2 is between 2.1 and 4.1 mm²·s⁻¹ Hept-Ad falls within this range with a kinematic viscosity of 3.22 mm²·s⁻¹. In contrast, the 40° C. kinematic viscosity of Non-Ad is slightly above the range at 4.85 mm²·s⁻¹. In both cases the viscosities of the alkyl diamondoid mixtures at 40° C. are significantly lower than those observed for pure mono-alkylated adamantanes of similar molecular weight.

The densities of the Non-Ad and Hept-Ad fuel mixtures were similar: 0.912 and 0.919 g/mL, respectively. These values can be compared to 1,3-DMA (0.902 g/mL) and ETMA (0.896 g/mL). Although these values are lower than JP-10 (0.935 g/mL), they are substantially higher than conventional jet and diesel fuels which have average densities of roughly 0.81 and 0.84 g/mL, respectively (see Table 1). Based on their density values, the NHOCs of mixtures Non-Ad and Hept-Ad were quite similar with values of 138.0 and 138.4 kBtu/gal, respectively. Although these values are lower than some of the pure alkyl adamantanes studied previously ($C_{12}$-$C_{15}$; 139.9-144.1 kBtu/gal), they are higher than that measured for ETMA (135.6 kBtu/gal) and 1,3-DMA (135.3 kBtu/gal). These values are also significantly higher than conventional fuels, including petroleum derived diesel fuel (~129 kBtu/gal) and Jet-A (~125 kBtu/gal). Therefore, Hept-Ad and Non-Ad could be blended with conventional fuels to enhance the range of jet aircraft and diesel powered vehicles, including unmanned aerial vehicles.

Another critical property for diesel fuels is the cetane number. The cetane number measured for a fuel is inversely related to its ignition delay. Diesel fuels with higher cetane numbers (shorter ignition delays) allow for more efficient fuel consumption, decreased emissions, and reduced engine knocking and wear. The DCNs of Non-Ad and Hept-Ad were measured by Ignition Quality Tester (IQT). Both Non-Ad and Hept-Ad exhibited acceptable values of 46.6 and 42.5, respectively. The slightly lower value for Hept-Ad is likely due to the shorter average chain length of the pendent alkyl chains. For comparison, the DCN of 1,3-DMA is 36.3.

A comparison of some basic properties of fuel mixtures of the present invention, compared with diesel #2, are included in Table I below.

TABLE 1

Key fuel properties of alkyl adamantanes synthesized from adamantane with nonane (Non-Ad) and heptane (Hept-Ad)

| Fuel | Density (g/mL) | NHOC [kBtu/gal (MJ/L)] | DCN | η (−20° C., mm²s⁻¹) | Viscosity (40° C., mm²s⁻¹) |
|---|---|---|---|---|---|
| Non-Ad | 0.912 | 138.0 (38.5) | 46.6 (0.5) | 60.6 | 4.85 |
| Hept-Ad | 0.919 | 138.4 (38.6) | 42.5 (0.6) | 20.5 | 3.22 |
| 1,3-DMA | 0.902 | 136.0 (37.9) | 36.3 (0.5) | NM | 2.79 |
| Jet A | ~0.81 | ~125 (34.8) | 40-50 | <8.0 | N/A |
| Diesel #2 | ~0.84 | ~129 (36.0) | 40-54 | N/A | 2.1-4.1 |
| JP-10 | 0.935 | 141.5 (39.4) | 20 | 8.8 | 2.29 |

Example 5

Purified alkyl-adamantane mixtures of the present invention may be used directly as high-density fuels or formulated with various conventional or renewable fuels to generate full-performance jet and diesel fuels. In embodiments, a blended fuel including the alkyl-adamantane mixtures of the present invention has a density of at least 0.775 g/mL and a NHOC of at least 120,000 Btu/gal. In embodiments, the blended fuel has a cetane number ranging from about 42 to about 50 and is comprised of about 1% to about 70% of at least one alkyl-adamantane mixture of the present invention.

The above Examples are for illustration purposes only and not to be used to limit any of the embodiments. Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for synthesizing an alkyl-adamantane mixture, comprising:
    providing a reaction mixture of a source of adamantane with at least one alkane and a Lewis acid catalyst;
    reacting the mixture by heating the reaction mixture to produce a mixture of alkyl adamantanes;
    removing unreacted at least one alkane by distillation; and
    removing unreacted adamantane via distillation, sublimation, or crystallization.

2. The method according to claim 1, wherein said source of adamantane comprises adamantane, one or more alkyl adamantanes, or combinations thereof.

3. The method according to claim 1, wherein said at least one alkane is an alkane or cycloalkane having from 2-40 carbon atoms.

4. The method according to claim 3, wherein said at least one alkane is n-hexane, n-heptane, n-octane, n-nonane, or n-decane.

5. The method according to claim 1, wherein said at least one alkane is selected from the group consisting of mineral spirits, naphtha, petroleum ether, kerosene, diesel fuel, vegetable derived triglycerides, animal derived triglycerides, vegetable derived fatty acids, animal derived fatty acids, methyl esters, synthetic paraffinic kerosenes, hydrotreated fatty acids, hydrotreated esters, and mixtures thereof.

6. The method according to claim 1, wherein the molar ratio of said at least one alkane:source of adamantane in the mixture is from about 2:1 to about 5:1.

7. The method according to claim 1, wherein the Lewis acid catalyst is present in the amount of from about 0.001-50 mol %.

8. The method according to claim 7, wherein the Lewis acid catalyst is $AlCl_3$, $AlBr_3$, $AlI_3$, metal triflates or metalloid triflates.

9. The method according to claim 7, wherein the Lewis acid catalyst is a heterogeneous acid.

10. The method according to claim 7, wherein the Lewis acid catalyst is a Lewis acidic ionic liquid.

11. The method according to claim 1, wherein the reaction mixture is heated at a temperature ranging between about ambient and about 200 degrees C.

12. The method according to claim 1, wherein the reaction mixture is heated for a time period from about 10 minutes to about 7 days.

13. The method according to claim 1, further comprising refining the alkyl adamantane mixture by fractional distillation to yield high density fuel blends.

14. An alkyl adamantane mixture produced by the method of claim 1.

15. The alkyl adamantane mixture of claim 14 having a cetane number greater than about 40.

16. The alkyl adamantane mixture of claim 14 comprising an alkyl adamantanes of C10-C12, C10-C13, C10-C14, C10-C15, C10-C16, or C10-C17.

17. The alkyl adamantane mixture of claim 14 having a density from about 0.90 to about 0.94 g/mL.

18. The alkyl adamantane mixture of claim 14 having a volumetric net heat of combustion greater than or equal to about 135.0 kBtu/gal.

19. A high density fuel comprised of about 1% to about 70% of at least one alkyl-adamantane mixture of claim 14.

20. The high density fuel of claim 19 having density of at least 0.775 g/mL and a NHOC of at least 120,000 Btu/gal.

* * * * *